(12) United States Patent
Chung et al.

(10) Patent No.: US 8,729,028 B2
(45) Date of Patent: *May 20, 2014

(54) NOGGIN-DERIVED PEPTIDE AND USE THEREOF

(75) Inventors: Young Ji Chung, Yongin-si (KR); Young Deug Kim, Siheung-si (KR); Eun Mi Kim, Gunpo-si (KR); Sang Su Song, Seoul (KR); Il Hong, Yongin-si (KR); Kyoung Mi Cho, Cheonan-si (KR); Su Mi Kim, Jeongeup-si (KR); Sang Min Han, Gunpo-si (KR)

(73) Assignee: Caregen Co., Ltd., Gunpo-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/145,390

(22) PCT Filed: Nov. 24, 2009

(86) PCT No.: PCT/KR2009/006930
§ 371 (c)(1),
(2), (4) Date: Sep. 7, 2011

(87) PCT Pub. No.: WO2010/085039
PCT Pub. Date: Jul. 29, 2010

(65) Prior Publication Data
US 2011/0312884 A1    Dec. 22, 2011

(30) Foreign Application Priority Data
Jan. 20, 2009  (KR) .................. 10-2009-0004668

(51) Int. Cl.
*A61K 38/03* (2006.01)
*C07K 4/00* (2006.01)

(52) U.S. Cl.
USPC .......... 514/20.7; 514/18.6; 530/324; 530/327

(58) Field of Classification Search
None
See application file for complete search history.

(56) References Cited

U.S. PATENT DOCUMENTS

| | | | |
|---|---|---|---|
| 5,821,124 A | 10/1998 | Valenzuela et al. | |
| 6,331,309 B1 * | 12/2001 | Jennings et al. | 424/422 |
| 8,497,241 B2 * | 7/2013 | Chung et al. | 514/6.9 |
| 2003/0170656 A1 | 9/2003 | Cen et al. | |

OTHER PUBLICATIONS

Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Guo et al. Protein tolerance to random amino acid change. Proc Natl Acad Sci U S A. Jun. 22, 2004;101(25):9205-10. Epub Jun. 14, 2004.*
Semevolos et al. Expression of bone morphogenetic protein-6 and -2 and a bone morphogenetic protein antagonist in horses with naturally acquired osteochondrosis. Am J Vet Res. Jan. 2004;65(1):110-5.*
Cray et al. Blocking bone morphogenetic protein function using in vivo noggin therapy does not rescue premature suture fusion in rabbits with delayed-onset craniosynostosis. Plast Reconstr Surg. Mar. 2011;127(3):1163-72.*
Kan et al. Inhibition of BMP signaling in P-Cadherin positive hair progenitor cells leads to trichofolliculoma-like hair follicle neoplasias. J Biomed Sci. Dec. 14, 2011;18:92.*
Levi et al. Enhancement of human adipose-derived stromal cell angiogenesis through knockdown of a BMP-2 inhibitor. Plast Reconstr Surg. Jan. 2012;129(1):53-66.*
Age spots (liver spots), by Mayo Clinic staff, [online], [retrieved on Dec. 26, 2012]. Retrieved from the internet: URL<http://www.mayoclinic.com/health/age-spots/DS00912>, Feb. 24, 2011.*
Wrinkles, by Mayo Clinic staff, [online] , [retrieved on Dec. 26, 2012]. Retrieved from the internet: URL<http://www.mayoclinic.com/health/wrinkles/DS00890>, Jan. 27, 2011.*
Inflammation, from Wikipedia, the free encyclopedia [online], [retrieved on Dec. 26, 2012]. Retrieved from the internet: URL<http://en.wikipedia.org/wiki/Inflammation>.*
Growth Factor, from Wikipedia, the free encyclopedia [online], [retrieved on Dec. 27, 2012]. Retrieved from the internet: URL<http://en.wikipedia.org/wiki/Growth_factor>.*

* cited by examiner

*Primary Examiner* — David Romeo
(74) *Attorney, Agent, or Firm* — Clark & Elbing LLP

(57) ABSTRACT

Disclosed are a noggin-derived peptide and a composition containing the same for promoting hair growth, improving skin conditions, providing anti-inflammatory function, or preventing or treating bone diseases. The disclosed noggin-derived peptide performs a function identical or similar to that of natural human noggin and is superior in stability and skin permeability as compared thereto. The composition containing the peptide of the present disclosure as an active ingredient exhibits remarkably superior effects in treating, preventing or improving growth factor-related symptoms, e.g. hair loss, skin conditions or cut, or treating, preventing or improving growth factor overexpression-related symptoms. Therefore, the superior activity and stability of the peptide of the present disclosure are greatly advantageous in application to medicine, quasi-drugs and cosmetics.

6 Claims, 10 Drawing Sheets

Keratinocyte

Control

Peptide

Fibroblast

Control

Peptide

SEQUENCE LISTING

```
<160> NUMBER OF SEQ ID NOS: 3

<210> SEQ ID NO 1
<211> LENGTH: 12
<212> TYPE: PRT
<213> ORGANISM: Homo sapiens

<400> SEQUENCE: 1

Glu Leu Ile Glu His Gly Gly Gly Arg Pro Ala Asp
1               5                   10

<210> SEQ ID NO 2
<211> LENGTH: 5
<212> TYPE: PRT
<213> ORGANISM: Homo sapiens

<400> SEQUENCE: 2

Glu Leu Ile Glu His
1               5

<210> SEQ ID NO 3
<211> LENGTH: 4
<212> TYPE: PRT
<213> ORGANISM: Homo sapiens

<400> SEQUENCE: 3

Arg Pro Ala Asp
1
```

NOGGIN-DERIVED PEPTIDE AND USE THEREOF

CROSS-REFERENCE TO RELATED APPLICATIONS

This application is the U.S. national stage filing under 35 U.S.C. §371 of international application PCT/KR2009/006930, filed Nov. 24, 2009, which claims benefit of Korean Patent Application 10-2009-0004668, filed Jan. 20, 2009.

TECHNICAL FIELD

The present disclosure relates to a noggin-derived peptide and a composition containing the same.

BACKGROUND

Hair follicle is a peculiar skin organ of mammals. At the base of the hair follicle is a large structure that is called papilla (Stenn and Paus, *Physiol. Rev.,* 81: 449 (2002)). The papilla is essential in normal circulation of the hair follicle (Oliver, *Embryol. Exp. Morph.* 15: 331 (1966); Oliver, *Embryol. Exp. Morph.* 16: 231 (1967)) and in growth of the hair shaft. The hair shaft is a thread-shaped structure prepared from epithelial cells, composed of keratin filaments and filament-aggregating proteins tightly attached thereto.

Human hair follows a growth cycle with three distinct phases: anagen, catagen, and telogen phases. The hair growth cycle is regulated by hormones or many growth factors. Severe stress or malnutrition may advance the catagen and telogen phases, leading to severe hair loss (alopecia) (Vladimir A. Botchkarev, *American Journal of Pathology,* 162 (3): 709-712 (2003)).

In male pattern baldness, the hair follicles at the front and top of the scalp are sensitive to androgen, which causes the follicles to shrink or miniaturize, thereby resulting in hair loss. In 20% of women, the hair often becomes thinner at the top of the scalp, resulting in "female pattern baldness". The hair loss broadens with aging. Also, cicatricial alopecia caused by injury, disease or burns may cause severe hair loss. Whatever is the cause, hair loss may have remarkable psychological, social and sexual impacts as well as loss of pride and self-respect. Although various drugs have been used to treat hair loss, they are too expensive or give very different results among individuals.

In cosmetic products, inexpensive but less effective plant extracts have been used, which do not give good result. To overcome these problems, keratinocyte growth factor derived from human has been produced in large scale through fermentation and purification using *E. coli,* and the nanosome technology has been developed to improve skin permeability. Also, the effect has been further improved by adding keratinocyte growth factor-derived peptides. Keratinocyte growth factor facilitates the anagen phase during which hair is produced and grows. It retains the hair cycle at the anagen, thereby reducing hair loss caused by various environmental factors, and, in normal hair, it contributes to the growth and health of hair by supplying nutrients. The treatment of and solution to hair loss have changed greatly with time. Although baldness can be covered using wigs or toupees or by expanding hair, they do not lead to hair regrowth. And, although the two currently available drugs (minoxidil and finasteride) known thus far can delay further hair loss, they do not induce regeneration of hair follicles. Many hair care cosmetics for preventing hair loss using plant extracts have been released in the market. Especially, the products using extracts of sophora, hot pepper, black pepper, mulberry root, mulberry leaf, ginseng, licorice, peony, foxglove, fennel, Japanese cornel, garlic, etc., the products prepared to improve cellular metabolism suppressed by excess dihydrotestosterone (DHT) and to facilitate hair regeneration and growth by adding compositions containing xanthines and growth hormones, the products prepared to supply nutrients to the scalp and hair and to prevent hair loss and promote hair growth by adding minerals, vitamins and extracts of green tea, rosemary, mugwort and licorice, and the male pattern baldness products prepared to suppress production of DHT during androgen metabolism by inhibiting 5-alpha reductases and to help hair metabolism by mixing the substances such as vitamin B, vitamin C, vitamin D, vitamin E, nicotinic acid, pantothenic acid, biotin, folic acid, etc. with plant extracts have been developed. But, they hardly affect the production of new hair. Also, the products inhibiting 5-alpha reductases and exhibiting excellent hair growth effect have been developed by using, for example, corosolic acid, which was shown to be effective in diabetes, etc. by a research group of the Jikei University School of Medicine in Tokyo, Japan.

Many factors are involved in the growth and degeneration of hair. The inventors of the present disclosure have studied the growth factors that promote hair production and growth by activating keratinocyte growth factors and vascular endothelial growth factors and suppressing activity of BMP proteins. In particular, they have produced noggin proteins, which suppress BMP2/4 that inhibits the human-derived keratinocyte growth factors FGF-7 (KGF) and FGF-10 involved in hair cycle and retards the initiation of anagen during the hair follicle growth, in large scale through fermentation and purification using *E. coli* and developed them into growth factor-containing cosmetics to promote hair growth and prevent hair loss (Korean Patent No. 1007968170000; Growth factor for hair and skin treatment). Although the growth factors provide excellent effect, additional process and time for refolding are required to obtain wild-type growth factors. Further, a complicated purification process is necessary to remove the source of contamination derived from *E. coli,* and the stability and high molecular weight problems as well as high cost make it less applicable.

In order to solve the problems associated with the expression of growth factors, there have been attempts to produce only part of some growth factors by solid-phase synthesis to achieve a similar function. For example, in U.S. Pat. No. 5,473,054, Jameson et al. have named the 29-38 and 61-70 fragments of IGF-1 respectively as JB2 and JB1, and reported the effect of the peptide fragments on cellular growth as well as the inhibitory effect of JB3, an enantiomer of JB1, against IGF-1. Also, Teruo et al. have reported in WO 03/048192 the complementary action of the 33-37 fragment of IGF-1 and a substance P-derived tetrapeptide in wound healing. In addition, Kodama et al. have reported in *Autoimmunity* 37: 481-487 (2004) that the 50-70 fragment of IGF-1 helps treatment of diabetes in mouse.

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THE INVENTION

The inventors of the present disclosure have prepared and screened out various peptides derived from human noggin in order to prepare a peptide being superior in stability and skin permeability to the natural growth factor noggin while performing a function identical or similar to that of the natural noggin. As a result, they have screened out, among the many candidate peptides, those providing superior physiological activity as well as superior stability and skin permeability.

The present disclosure is directed to providing a peptide exhibiting a growth factor activity.

The present disclosure is also directed to providing a composition for promoting hair growth.

The present disclosure is also directed to providing a composition for improving skin conditions.

The present disclosure is also directed to providing an anti-inflammatory composition.

The present disclosure is also directed to providing a composition for preventing or treating bone diseases.

Other features and aspects will be apparent from the following detailed description, drawings, and claims.

In one general aspect, the present disclosure provides a peptide exhibiting a growth factor activity, comprising an amino acid sequence represented by the general formula (1):

$$\text{Glu-Leu-Ile-Glu-His (SEQ ID NO: 2)-linker-Arg-Pro-Ala-Asp (SEQ ID NO: 3)} \quad (1)$$

In another general aspect, the present disclosure provides a composition for promoting hair growth containing the peptide exhibiting a growth factor activity as an active ingredient.

In another general aspect, the present disclosure provides a composition for improving skin conditions containing the peptide exhibiting a growth factor activity as an active ingredient.

In another general aspect, the present disclosure provides an anti-inflammatory composition containing the peptide exhibiting a growth factor activity as an active ingredient.

In another general aspect, the present disclosure provides a composition for preventing or treating bone diseases containing the peptide exhibiting a growth factor activity as an active ingredient.

The inventors of the present disclosure have prepared and screened out various peptides derived from human noggin in order to prepare a peptide being superior in stability and skin permeability to the natural growth factor noggin while performing a function identical or similar to that of the natural noggin. As a result, they have screened out, among the many candidate peptides, those providing superior physiological activity as well as superior stability and skin permeability.

The inventors of the present disclosure have randomly synthesized several parts of the growth factor noggin and explored the sites capable of binding to the receptor protein. Then, by optimizing the amino acid sequence of the expected portions, they have prepared candidate peptides, among which those presenting the best activity were screened out as the peptide of the present disclosure.

The peptide of the present disclosure comprises an amino acid sequence represented by the general formula (1). Specifically, the peptide of the present disclosure essentially consists of the amino acid sequence represented by the general formula (1). Most specifically, the peptide of the present disclosure consists of the amino acid sequence represented by the general formula (1).

In amino acid sequence represented by the general formula (1), noggin-derived sequences at N- and C-termini are linked by a linker.

The linker used in the present disclosure may be those commonly used in the art. The linker may have a length and/or sequence specially selected to maximize the activity of the present disclosure peptide, i.e. the noggin activity.

Specifically, the linker may comprise a plurality of amino acid residues. Linkers comprising amino acid sequences are described in Huston, et al., *Methods in Enzymology*, 203: 46-88 (1991) and Whitlow, et al., *Protein Eng.*, 6: 989 (1993), which are incorporated herein by reference. A linker suitable for the present disclosure mainly comprises glycine or glycine and serine amino acid residues, and is 2-18 amino acids long. In a specific embodiment of the present disclosure, the linker comprises a plurality of amino acid residue. In a more specific embodiment of the present disclosure, the linker comprises 2 to 10 Gly residues, more specifically 2 to 7 Gly residues, most specifically 3 Gly residues.

The peptide of the present disclosure has better stability than natural noggin as it is, but its stability may be further improved through amino acid modification.

In a specific embodiment of the present disclosure, the N-terminus or the C-terminus of the peptide may be bound to a protecting group selected from a group consisting of an acetyl group, a fluorenylmethoxycarbonyl group, a formyl group, a palmitoyl group, a myristyl group, a stearyl group, a polyethylene glycol (PEG) and an amino acid.

In a specific embodiment of the present disclosure, the C-terminus of the peptide may be modified with a hydroxyl (—OH) group or an amino (—NH$_2$) group.

The stability of the peptide of the present disclosure may be greatly improved by the amino acid modification. As used herein, the term "stability" refers not only to in vivo stability but also to storage stability (e.g., storage stability at room temperature). The protecting group protects the peptide of the present disclosure from attack by proteolytic enzymes.

As used herein, the term "peptide" refers to a linear-chain molecule wherein amino acid residues are linked by peptide bonds. The peptide of the present disclosure may be prepared according to known chemical synthesis techniques, especially the solid-phase synthesis techniques (Merrifield, *J. Amer. Chem. Soc.* 85: 2149-54 (1963); Stewart, et al., *Solid Phase Peptide Synthesis*, 2nd. ed., Pierce Chem. Co.: Rockford, 111 (1984)).

The peptide of the present disclosure has an activity identical or similar to that of the natural growth factor noggin.

In a specific embodiment of the present disclosure, the peptide of the present disclosure has an ability to promote cellular growth. In a specific embodiment of the present disclosure, the peptide of the present disclosure peptide promotes the production of laminin or hyaluronic acid.

In a specific embodiment of the present disclosure, the peptide of the present disclosure exhibits an antagonistic activity against bone morphogenetic protein (BMP)-2, BMP-4 or BMP-7 by binding to BMP-2, BMP-4 or BMP-7. That is to say, the peptide of the present disclosure exhibits an antagonistic activity by strongly binding to BMP-2, BMP-4 and/or BMP-7 and thus preventing them from binding with their receptors.

More specifically, the peptide of the present disclosure exhibits a prophylactic or therapeutic effect for a disease, disorder or condition wherein BMP-2, BMP-4 or BMP-7 is involved, and the disease, disorder or condition is hair loss, inflammatory or bone disease.

As used herein, the term "disease, disorder or condition wherein BMP-2, BMP-4 or BMP-7 is involved" refers to a pathological condition caused by the overexpression of BMP-2, BMP-4 or BMP-7.

It is well known in the art that BMP-2, BMP-4 and BMP-7 are involved in various pathological conditions such as hair loss, inflammatory or bone disease (Kanami I, et al., Bone Morphogenetic Protein 2 Stimulates Osteoclast Differentiation and Survival Supported by Receptor Activator of Nuclear Factor-κB Ligand, *Endocrinology*, 142 (8): 3656-662 (2001); US Patent Application No. 20060276385; and WO 99/61044). Therefore, the peptide of the present disclosure exhibiting an antagonistic activity against BMP-2, BMP-4 or BMP-7 is effective in preventing or treating a disease wherein BMP-2, BMP-4 or BMP-7 is involved.

In another general aspect, the present disclosure provides a composition for promoting hair growth comprising the peptide exhibiting a growth factor activity as an active ingredient.

Noggin is a polypeptide that inhibits transforming growth factor (TGF-β) signal transduction by binding to TGF-β family ligands. Like other TGF-β inhibitors such as chordin or follistatin, noggin inhibits the activity of BMPs, particularly BMP-2, BMP-4 and BMP-7, expressed at the hair follicle (*American Journal of Path.*, Vol. 165, No. 3: 729-740 (2004)).

In an embodiment of the present disclosure, the peptide of the present disclosure is derived from human noggin and greatly enhances hair growth in animal experiment (FIG. 10).

As used herein, the terms "promoting hair growth" and "preventing hair loss" are used synonymously.

In a specific embodiment of the present disclosure, the hair loss prevented or treated by the composition of the present disclosure includes alopecia areata, alopecia totalis, alopecia universalis, androgenic alopecia (male pattern baldness), telogen effluvium, anagen effluvium or chemotherapy-induced alopecia, but is not limited thereto (Cotsarelis et al., Towards a molecular understanding of hair loss and its treatment, *Trends in Mol. Med.*, 7: 293-301 (2001); MacDonald, N., Alopecia areata: identification and current treatment approaches, *Dermatol. Nurs.*, 11: 356-359 (1999)).

In another general aspect, the present disclosure provides a composition for improving skin conditions comprising the peptide exhibiting a growth factor activity as an active ingredient.

In a specific embodiment of the present disclosure, the improvement of skin conditions includes improvement of wrinkles, improvement of skin elasticity, prevention of skin aging, improvement of skin moisturization, removal of age spots, or healing of cuts. As demonstrated in the following examples, the peptide of the present disclosure can improve various skin conditions by facilitating proliferation of keratinocytes and fibroblasts and promoting production of laminin and hyaluronic acid.

In another general aspect, the present disclosure provides a composition for preventing or treating a disease, disorder or condition wherein BMP-2, BMP-4 or BMP-7 is involved, comprising the peptide inhibiting BMP activity as an active ingredient.

The peptide of the present disclosure exhibits an antagonistic activity against BMP proteins, particularly BMP-2, BMP-4 and BMP-7, by binding to BMP-2, BMP-4 and BMP-7.

In a specific embodiment of the present disclosure, the disease, disorder or condition prevented or treated by the antagonistic activity of the peptide of the present disclosure is inflammatory or bone disease.

Various inflammatory diseases may be prevented or treated by the peptide of the present disclosure. Non-limiting examples include encephalitis, inflammatory bowel disease, chronic obstructive pulmonary disease, allergy, septic shock, pulmonary fibrosis, undifferentiated spondyloarthropathy, undifferentiated arthropathy, arthritis, inflammatory osteolysis, and chronic inflammation caused by viral or bacterial infection.

Various bone diseases may be prevented or treated by the peptide of the present disclosure. Non-limiting examples include osteoarthritis, rheumatoid arthritis, bone damage caused by bone metastasis of cancer cells, osteoporosis, osteomalacia, rickets, osteitis fibrosa, aplastic bone disease, metabolic bone disease, osteolysis, leukopenia, bone deformity, hypercalcemia, or nerve compression syndrome.

Since the compositions of the present disclosure comprise the noggin-derived peptide of the present disclosure described above as an active ingredient, a detailed description thereof will not be given again.

In a specific embodiment of the present disclosure, the composition of the present disclosure is a pharmaceutical composition comprising: (a) a pharmaceutically effective amount of the noggin-derived peptide of the present disclosure described above; and (b) a pharmaceutically acceptable carrier.

As used herein, the term "pharmaceutically effective amount" refers to an amount sufficient to achieve the effect or activity of the noggin-derived peptide described above.

The pharmaceutically acceptable carrier included in the pharmaceutical composition of the present disclosure may be one commonly employed in the art. Non-limiting examples include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc. The pharmaceutical composition of the present disclosure may further include, in addition to above-described components, a lubricant, a wetting agent, a sweetener, a fragrance, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present disclosure may be administered orally or parenterally. For parenteral administration, it may be administered intravenously, subcutaneously, intramuscularly, intraabdominally, transdermally, or the like.

An appropriate dosage of the pharmaceutical composition of the present disclosure may be determined variously depending on such factors as preparation method, administration method, age, body weight and sex of the patient, pathological condition, diet, administration time, administration route, excretion rate or response sensitivity. A recommended dosage of the pharmaceutical composition of the present disclosure is 0.0001-100 μg per day.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, emulsion, extract, powder, granule, tablet, capsule or gel (e.g., hydrogel), and may further include a dispersant or stabilizer.

In a specific embodiment of the present disclosure, the composition of the present disclosure is a cosmetic composition comprising: (a) a cosmetically effective amount of the noggin-derived peptide of the present disclosure described above; and (b) a pharmaceutically acceptable carrier.

As used herein, the term "cosmetically effective amount" refers to an amount sufficient of the composition of the present disclosure to achieve improvement of skin conditions.

The cosmetic composition of the present disclosure may be formulated into any form commonly used in the art. Non-limiting examples include solution, suspension, emulsion, paste, gel, cream, lotion, powder, soap, surfactant-containing cleanser, oil, powder foundation, emulsion foundation, wax foundation, spray, etc. More specifically, it may be prepared into soothing lotion, nourishing lotion, nourishing cream, massage cream, essence, eye cream, cleansing cream, cleansing foam, cleansing water, pack, spray or powder.

When the composition of the present disclosure is in the form of paste, cream or gel, animal oil, plant oil, wax, paraffin, starch, tragacanth, cellulose derivatives, polyethylene glycol, silicone, bentonite, silica, talc, zinc oxide, etc. may be used as the carrier.

When the composition of the present disclosure is in the form of powder or spray, lactose, talc, silica, aluminum hydroxide, calcium silicate or polyamide powder may be used as the carrier. Especially, the spray may further comprise a propellant such as hydrochlorofluorocarbon, propane/butane or dimethyl ether.

When the composition of the present disclosure is in the form of solution or emulsion, a solvent, solubilizer or emulsifier may be used as the carrier, examples of which include water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester.

When the composition of the present disclosure is in the form of suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as the carrier.

When the composition of the present disclosure is in the form of surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oil, lanolin derivatives, ethoxylated glycerol fatty acid ester, etc. may be used as the carrier.

In addition to the peptide as the active ingredient and the carrier ingredients, the cosmetic composition of the present disclosure may further comprise those ingredients commonly used in cosmetic compositions. Examples include common adjuvants such as antioxidant, stabilizer, solubilizer, vitamin, pigment and fragrance.

The features and advantages of the present disclosure may be summarized as follows:

(a) The noggin-derived peptide of the present disclosure may function identically or similarly to the natural human noggin.

(b) The peptide of the present disclosure provides better stability than the natural noggin and exhibits excellent skin permeability.

(c) The composition comprising the peptide of the present disclosure as an active ingredient is very effective in treating, preventing or improving growth factor-related symptoms, e.g. hair loss, skin conditions or cut, or treating, preventing or improving growth factor overexpression-related symptoms.

(d) The superior activity and stability of the peptide of the present disclosure are greatly advantageous in application to medicine, quasi-drugs and cosmetics.

BRIEF DESCRIPTION OF THE DRAWINGS

FIG. 8b shows a western blot for identifying the binding ability of a peptide prepared according to the present disclosure to the BMP-4 protein. The standard proteins on the right side are identical to the elution fractions in FIG. 8a.

Figure 1:
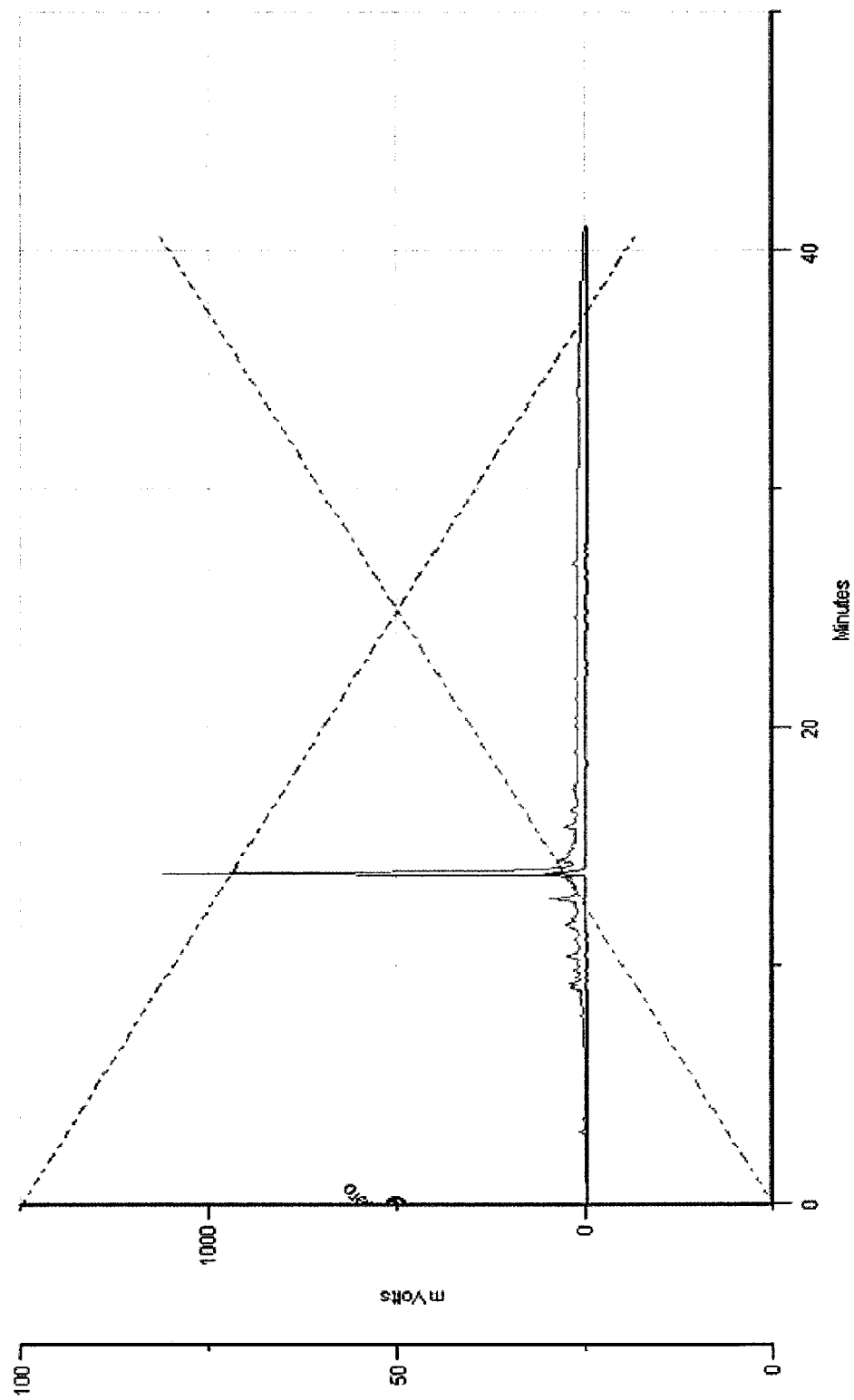
FIG. 1 shows a high-performance liquid chromatography analysis result of a peptide synthesized according to the present disclosure.

The examples and experiments will now be described. The following examples and experiments are for illustrative purposes only and not intended to limit the scope of this disclosure.

EXAMPLES

Synthesis Example

Synthesis of Glu-Leu-Ile-Glu-His (SEQ ID NO:2)-Linker-Arg-Pro-Ala-Asp (SEQ ID NO:3)

700 mg of chlorotrityl chloride (CTL) resin (Nova Biochem, Cat No. 01-64-0021) was put in a reactor and stirred for 3 minutes after adding 10 mL of methylene chloride (MC). After removing the solvent, 10 mL of dimethylformamide (DMF) was added. Then, after stirring for 3 minutes, the solvent was removed again. After adding 10 mL of dichloromethane (DCM) to the reactor, 200 mmol of Fmoc-Asp(tBu)-OH (Bachem, Swiss) and 400 mmol of diisopropylethylamine (DIEA) were added and dissolved well by stirring. After reacting for 1 hour with stirring, the mixture was washed and dissolved with methanol and DIEA (2:1) in DCM. After reaction for 10 minutes, the mixture was washed with excess DCM/DMF (1:1). After removing the solvent, followed by addition of 10 mL of DMF and stirring for 3 minutes, the solvent was removed again. After adding 10 mL of a deprotecting solution (20% piperidine in DMF) to the reactor, the mixture was stirred for 10 minutes at room temperature and then the solution was removed. After adding again the same amount of the deprotecting solution and performing reaction for 10 minutes, the solution was removed and Asp(tBu)-CTL resin was prepared by washing twice with DMF, once with MC, and once with DMF, for 3 minutes each. After adding 10 mL of DMF to another reactor, 200 mmol of Fmoc-Ala-OH (Bachem, Swiss), 200 mmol of HoBt and 200 mmol of Bop were added and dissolved well by stirring. After adding 400 mmol of DIEA to the reactor in two fractions, the mixture was stirred for at least 5 minutes until all the solid was dissolved. The resulting amino acid mixture solution was added to the reactor containing the deprotected resin and reacted for 1 hour at room temperature with stirring. After removing the reaction solution, followed by stirring with DMF solution 3 times, 5 minutes each, the solution was removed. A small amount of the reacted resin was taken and subjected to Kaiser test (nihydrin test) to determine the extent of reaction. Ala-Asp(tBu)-CTL resin was prepared in the same way as described above by deprotecting 2 times with the deprotecting solution. After sufficiently washing with DMF and MC and carrying out Kaiser test once again, amino acid attachment was carried out as follows in the same way as described above. According to the selected amino acid sequence, chain reaction was carried out in the order of Fmoc-Pro, Fmoc-Arg(pbf), linker (Gly, Gly-Gly, Gly-Gly-Gly, Gly (4), aminobutyric acid, aminobenzoic acid), Fmoc-His(trt), Fmoc-Glu(OtBu), Fmoc-Ile, Fmoc-Leu and Fmoc-Glu(tBu). After reacting the Fmoc-protecting group with the deprotecting solution twice for 10 minutes each, the solution was removed by washing well. After performing acetylation for an hour by adding acetic anhydride, DIEA and HoBt, the prepared peptidyl resin was washed 3 times, each with DMF, MC and methanol, dried by slowly flowing nitrogen gas, completely dried in the presence of $P_2O_5$ under reduced pressure, reacted with 30 mL of a leaving solution (containing trifluroacetic acid 95%, distilled water 2.5% and thioanisole 2.5%) for 2 hours at room temperature upon intermittent agitation. The resin was filtered and washed with a small volume of TFA solution, after which the filtrate was combined with the mother liquor. After distillation under reduced pressure to reduce the total volume to about half, precipitation was induced by adding 50 mL of cold ether and the formed precipitates were collected by centrifugation, followed by washing twice with cold ether. After removing the mother liquor, the resultant was dried sufficiently under nitrogen atmosphere to obtain 1.11 g of unpurified Glu-Leu-Ile-Glu-His (SEQ ID NO:2)-Linker-Arg-Pro-Ala-Asp (SEQ ID NO:3) peptide (linker=Gly-Gly-Gly) (SEQ ID NO:1) (yield: 88.2%). The molecular weight was measured as 1250.9 (theoretical value: 1250.35) using a molecular weight analyzer.

TABLE 1

| SEQ ID NO | Amino acid sequence | Molecular weight | |
|---|---|---|---|
| | | Measured value | Theoretical value |
| 1 | ELIEH-Linker-RPAD (linker = Gly-Gly-Gly; SEQ ID NO: 1) | 1250.9 | 1250.35 |

Test Example 1

Effect of Synthesized Peptide on Cellular Growth

To analyze the growth factor-like effect of the peptide synthesized in Synthesis Example, sulforhodamine B (SRB) calorimetric assay was carried out using HaCaT keratinocytes (Korean Cell Line Bank) and NIH3T3 fibroblasts (Korean Cell Line Bank) according to Rizzino et al.'s method (Rizzino et al. *Cancer Res.* 48: 4266 (1988)).

HaCaT keratinocytes and NIH3T3 fibroblasts were cultured respectively in a 250-mL tissue culture flask in Eagle's minimal essential media (EMEM; Gibco, U.S.A.) containing 10% fetal bovine serum (FBS; Sigma). The cultured cells were treated with 0.25% trypsin solution to detach the cells from the bottom of the culture flask and centrifuged to collect cell pellets. They were resuspended in FBS-free EMEM and added to each well of a 96-well tissue culture plate, with $4 \times 10^3$ cells per well. The cells were cultured under 7% $CO_2$ for 24 hours at 37° C. 24 hours later, the medium was changed with fresh, FBS-containing medium and the cells were incubated for 72 hours under the same conditions as described above with blank sample as reference or with the sterilized synthetic peptide (100 ng/mL) dissolved in water and 10% DMSO. After removing the supernatant, the cells were washed once with phosphate buffered saline (PBS). After removing the washing solution and treating with SRB solution, followed by sufficient washing with PBS, the cells were observed under a microscope to evaluate cell viability. In addition, absorbance was measured at 590 nm to analyze cell proliferation.

Figure 2A:
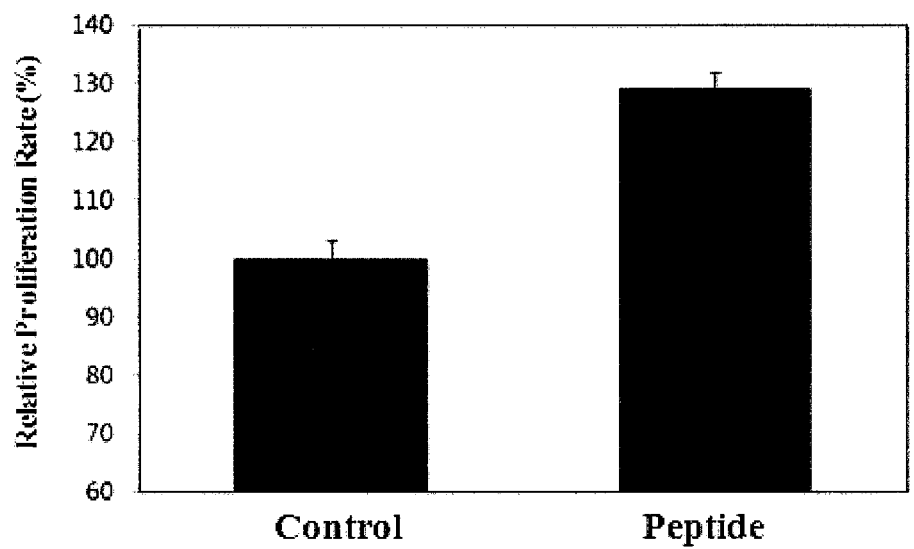
FIG. 2a shows a cellular growth rate of keratinocytes treated with a peptide synthesized according to the present disclosure.
Figure 2B:
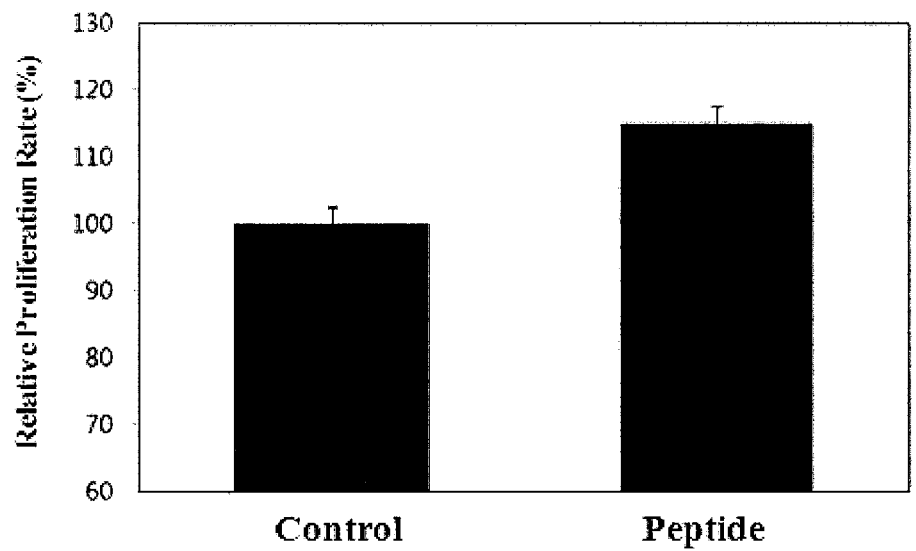
FIG. 2b shows a cellular growth rate of fibroblasts treated with a peptide synthesized according to the present disclosure.
Figure 3:
FIG. 3 shows microscopic images showing the cellular growth promoting effect in keratinocytes and fibroblasts treated with a peptide of the present disclosure.
Figure 3:
Figure 3:
Figure 3:
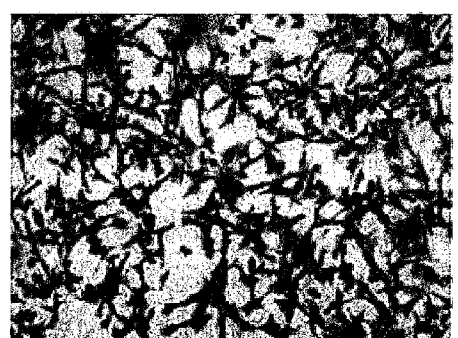

FIGS. 2a and 2b show the growth state of the keratinocytes (FIG. 2a) and fibroblasts (FIG. 2b) after treatment with the peptide, and FIG. 3 shows the microscopic images of surviving keratinocytes and fibroblasts 72 hours after the treatment with the peptide.

As seen from FIGS. 2a and 2b, the peptide of SEQ ID NO: 1 according to the present disclosure promote the growth of the keratinocytes and fibroblasts. From FIG. 3, it can be seen that the peptide of SEQ ID NO: 1 of the present disclosure promotes the growth of keratinocytes and fibroblasts.

Test Example 2

Laminin and Hyaluronic Acid Production Promoting Effect of Synthesized Peptide

Figure 4A:
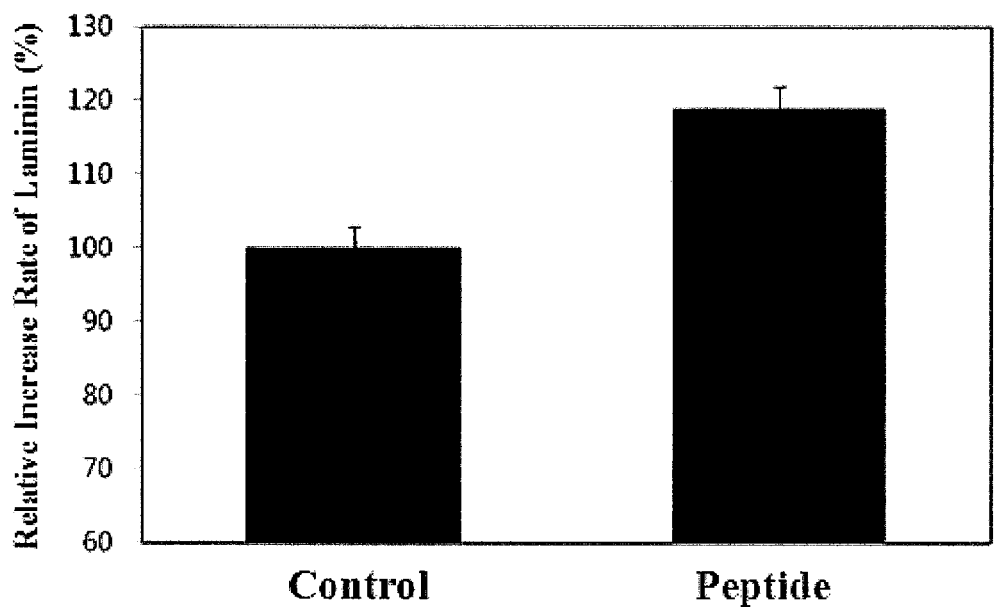
FIG. 4a shows increased production of laminin in fibroblasts treated with a peptide of the present disclosure.
Figure 4B:
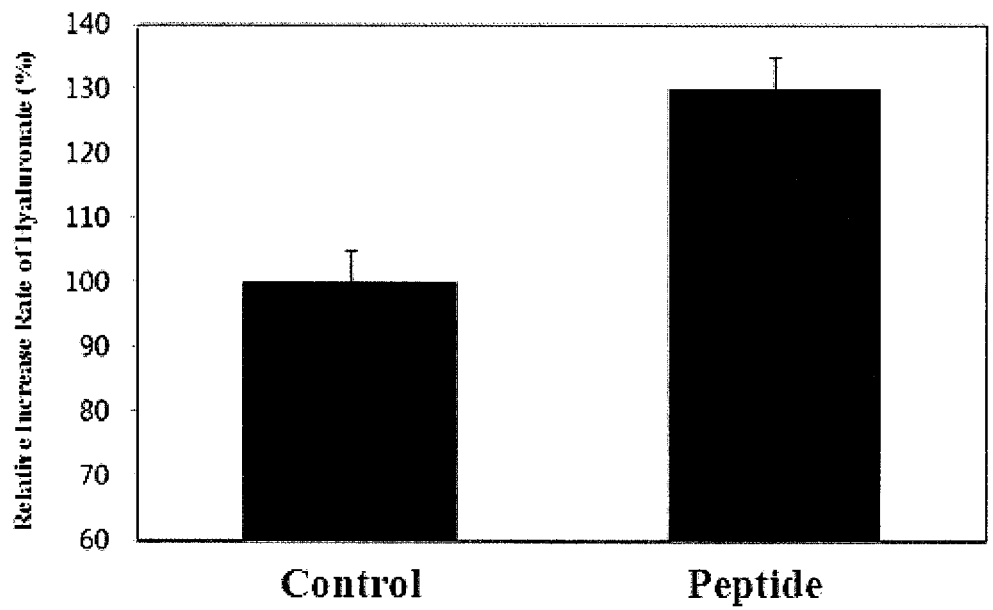
FIG. 4b shows increased production of hyaluronic acid in fibroblasts treated with a peptide of the present disclosure.

HaCaT cells cultured for 48 hours were treated with the peptide synthesized in Synthesis Example. 72 hours later, the level of laminin and hyaluronic acid was measured as an indicator to show the improvement in skin wrinkles. The measurement was made using a laminin ELISA kit (Takara, Japan) and a hyaluronic acid ELISA kit (Takara, Japan). It was revealed that the peptide of SEQ ID NO: 1 of the present disclosure increases the production of laminin (FIG. 4a) and hyaluronic acid (FIG. 4b) in fibroblasts.

To conclude the results of Test Examples 1 and 2, it can be seen that the peptide of SEQ ID NO: 1 of the present disclosure exhibits superior effect of skin improvement.

Test Example 3

Reduction of Melanin Pigment by Synthesized Peptide

Figure 5:
FIG. 5 shows a result of comparing production of melanin by B16 melanoma cells treated with α-MSH, after treating with a peptide prepared according to the present disclosure.

In order to investigate the antagonistic activity of the peptide synthesized in Synthesis Example against the growth factor BMP-4, C57BL/6 mouse melanocytes (Jung Ang Lab. Animal, Korea) were cultured and melanin production was induced with α-melanocyte stimulating hormone (α-MSH; Sigma). Then, after treating with BMP-4 (R&D Systems, Inc., USA) and then immediately with the synthesized peptide at different concentrations, it was checked whether the melanin production inhibited by BMP was activated again. The mouse melanocytes were cultured using DMEM (Sigma) containing 10% FBS (Sigma) at 37° C. under 5% $CO_2$. After culturing the cells on a 24-well plate at $1 \times 10^5$ cells/well and confirming attachment of the cells, the cells were treated only with a solvent (control), with 200 μg/mL α-MSH (positive control) or with 1 μg/mL BMP-4. Then, the cells were treated with the peptide of SEQ ID NO: 1. After adding the test substance to each dish, the cells were cultured for 3 days. The test substance had been prepared by dissolving the ingredients in a solvent and diluting to the test concentration using a 5:3:2 mixture solvent of propylene glycol:ethanol:purified water. After removing the medium by centrifugation, the production of melanin could be observed with naked eyes. As seen from FIG. 5, the α-MSH-treated group showed abrupt increase in melanin production. The peptide-treated group showed melanin production comparable to that of the α-MSH-treated group. This indicates that the treatment with the peptide appropriately inhibits the BMP-4 activity and thus increases melanin production.

Figure 6:
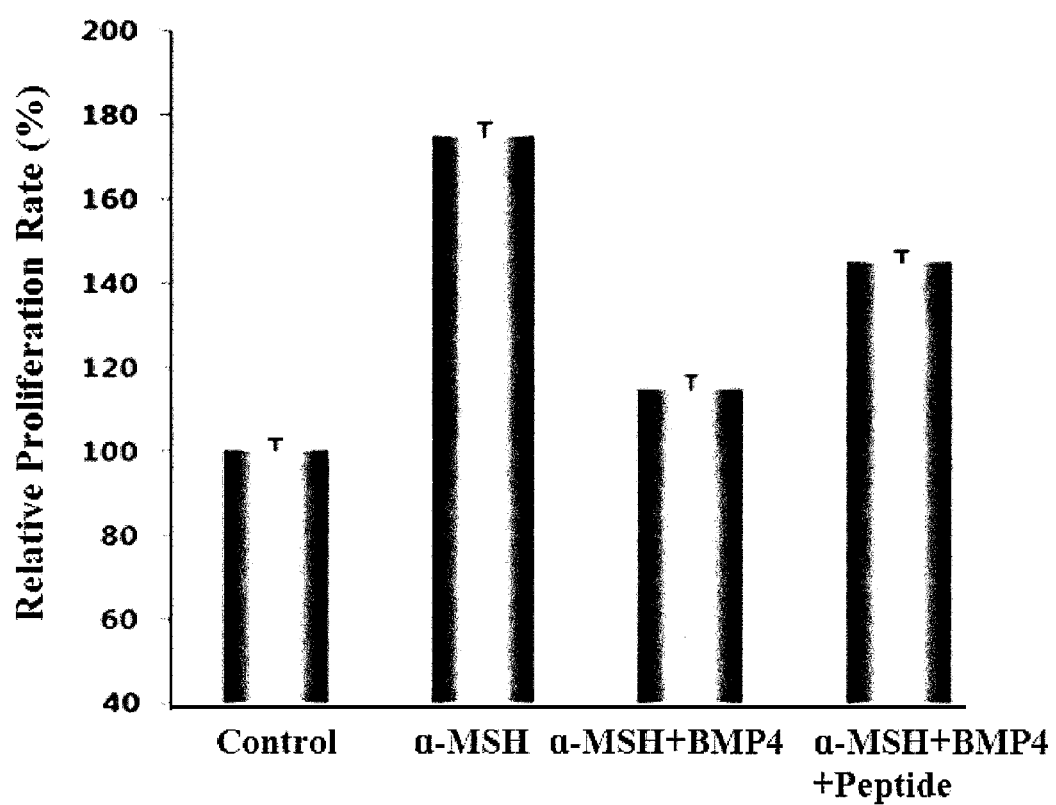
FIG. 6 shows production of melanin by B16 melanoma cells treated with α-MSH, after UV radiation.

For more accurate measurement, cells were washed with PBS and lysed with 1 N sodium hydroxide. Then, after measuring absorbance at 400 nm, inhibition of melanin production was calculated according to the Dooley's method (Dooley, T. P. et al., *Skin Pharmacol.* 7: 188-200 (1994)), and the result was shown in FIG. 6. The result shown in FIG. 6 coincides with that of FIG. 5.

Test Example 4

Binding of Synthesized Peptide to BMP4

In order to investigate whether the peptide synthesized according to the present disclosure binds to the BMP protein, the Biacore instrument allowing the detection of binding between drugs and receptors was used.

Figure 7:
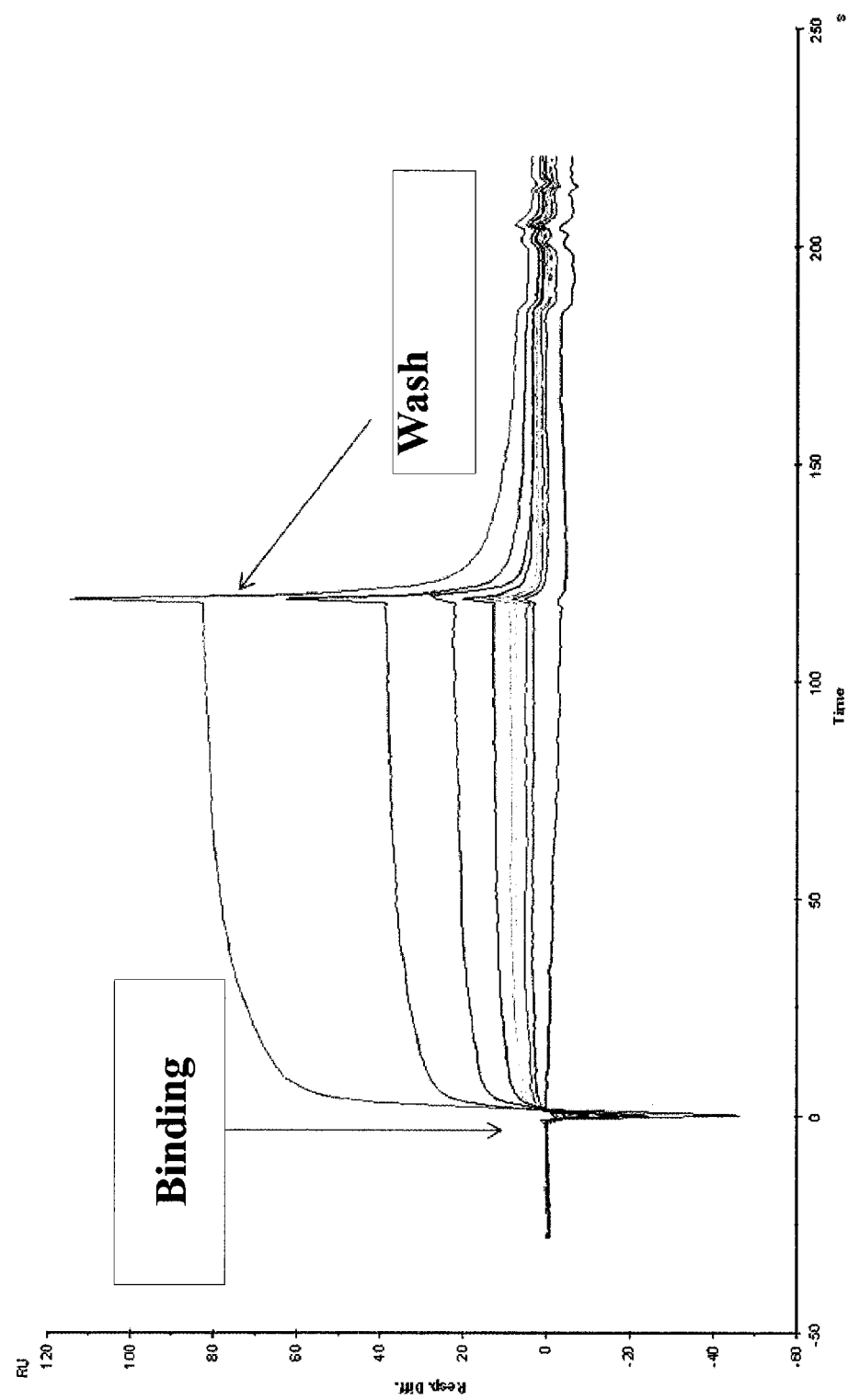
FIG. 7 shows a Biacore test result for identifying the binding ability of a peptide prepared according to the present disclosure to the BMP-4 protein.

6000 response units (RU) of rh-BMP4 protein (R&D Systems, Inc., USA) was fixed to a commercially available CM5 sensor chip (Biacore, Sweden) by amination. Then, HBS-EP buffer (Biacore, Sweden) was flown at a rate of 5 μL/min to activate the BMP4 protein on the CM5 sensor chip. After optimization for reaction, the synthesized peptide was flown at different concentrations (1000 μg/mL, 500 μg/mL, 250 μg/mL, 125 μg/mL, 62.5 μg/mL, 31.3 μg/mL, 15.6 μg/mL, 7.8 μg/mL, 4 μg/mL). The binding between BMP4 and the synthetic peptide could be identified from the increase in RU value. As shown in FIG. 7, the BMP4 protein and the synthetic peptide showed very strong binding ability. This suggests that the peptide of SEQ ID NO: 1 has an antagonistic activity against BMP-4.

Test Example 5

Immunobinding Between Synthesized Peptide and BMP Protein

Figure 8A:
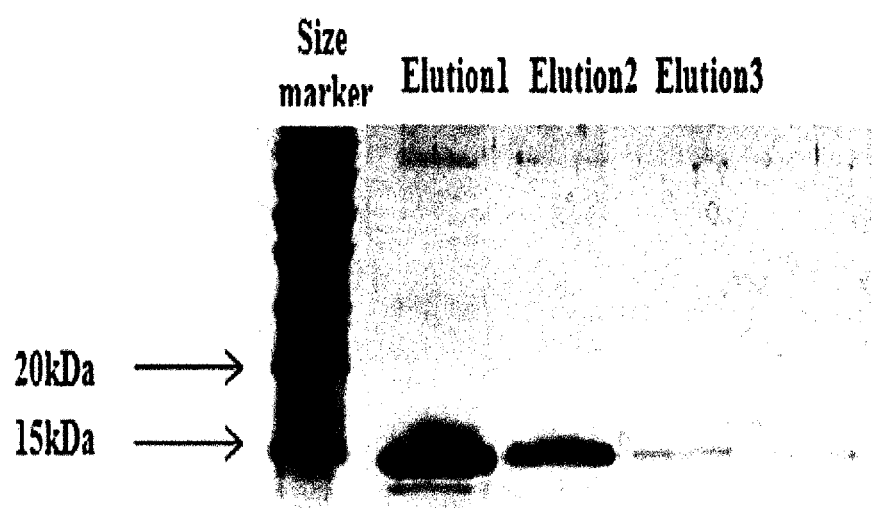
FIG. 8a shows an SDS-PAGE result for identifying the binding ability of a peptide prepared according to the present disclosure to the BMP-4 protein. Elution 1, Elution 2 and Elution 3 are fractions obtained sequentially by eluting with 0.5 M NaCl and 50 mM ammonium phosphate (pH 4.0) solutions. The protein size of the size markers (SM) is 100, 70, 50, 40, 30, 20 and 15 kDa.
Figure 8B:
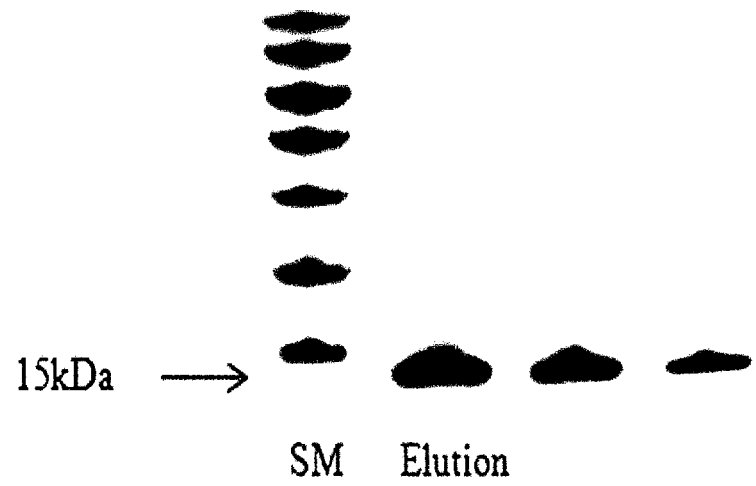

The N-terminus of the peptide prepared in Synthesis Example was modified with biotin (Sigma, USA). For streptavidin chromatography, the biotinylated peptide was loaded in in a column packed with streptavidin-attached resin and equilibrated with 20 mM sodium phosphate buffer. Then, after flowing rh-BMP4 protein (R&D Systems, Inc., USA) through the column, 200 mM sodium phosphate buffer was flown to flush unbound protein and the protein bound to the biotinylated peptide was fractionated by eluting with 0.2 M NaCl. The eluate was analyzed by SDS-PAGE (see FIG. 8*a*) and it was confirmed whether the BMP4 protein binds with the biotinylated peptide by western blotting using anti-BMP4 antibody (Santa Cruz, USA) (see FIG. 8*b*). As seen from FIG. 8*b*, the BMP4 protein was bound to the biotinylated peptide. This suggests that the BMP4 protein very strongly binds to the peptide of SEQ ID NO: 1.

Test Example 6

Thermal Stability of Synthesized Peptide

Figure 9:
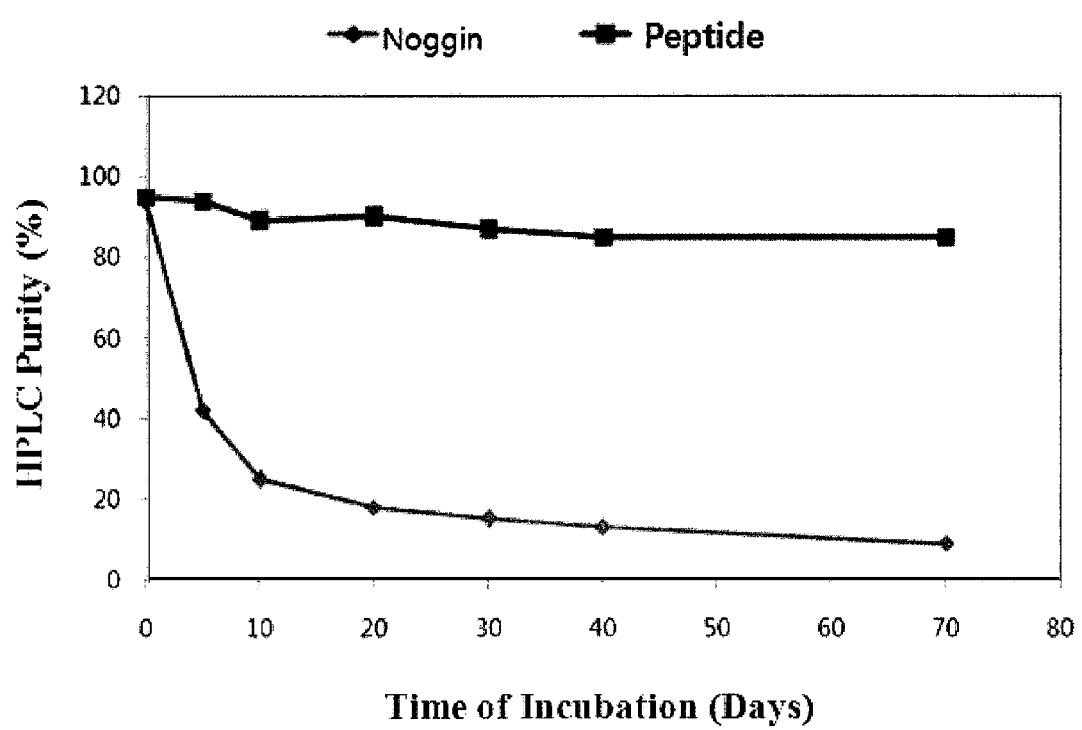
FIG. 9 compares the thermal stability of a peptide of the present disclosure.

The peptide prepared in Synthesis Example and a reference growth factor (Noggin, FGF-10) purchased from NIBSC (UK) were prepared to 0.11 mg/mL phosphate buffer solutions. 1 mL of each prepared solution was put in a glass vial and kept at 37° C. The solution was sampled on days 0, 5, 10, 20, 30, 40 and 70. After centrifugation to remove any denatured peptide or protein, the supernatant was subjected to HPLC for quantification (FIG. 9). As seen from FIG. 9, the peptide of the present disclosure exhibited much superior thermal stability to the existing noggin peptide.

Example 2

Preparation of Nanopeptide 50 mg of the peptide prepared in Synthesis Example was precisely weighed and dissolved in 500 mL of distilled water by sufficiently shaking. The resulting solution was mixed with 5 g of lecithin, 0.3 mL of sodium oleate, 50 mL of ethanol and a small amount of oil, and then the volume was adjusted to 1 L with distilled water. The solution was prepared into 100-nm sized nanosomes under high pressure using a microfluidizer. The final concentration of the prepared nanosomes was about 50 ppm and they were used as ingredients for cosmetics.

Formulation Example 1

Soothing Lotion

Soothing lotion containing the peptide nanosomes prepared in Example 2 was prepared according to a commonly employed method as follows.

TABLE 2

| Ingredients | Content (wt %) |
|---|---|
| Peptide nanosomes | 0.001 |
| 1,3-Butylene glycol | 6.0 |
| Glycerine | 4.0 |
| PEG 1500 | 1.0 |
| Sodium hyaluronate | 1.0 |
| Polysorbate 20 | 0.5 |
| Ethanol | 8.0 |
| Preservative and pigment | adequate |
| Benzophenone-9 | 0.05 |
| Perfume | trace |
| Purified water | residual |
| Total | 100 |

Formulation Example 2

Nourishing Cream

Nourishing cream containing the peptide nanosomes prepared in Example 2 was prepared according to a commonly employed method as follows.

TABLE 3

| Ingredients | Content (wt %) |
| --- | --- |
| Peptide nanosomes | 0.001 |
| Meadowfoam oil | 3.0 |
| Cetearyl alcohol | 1.5 |
| Stearic acid | 1.5 |
| Glyceryl stearate | 1.5 |
| Liquid paraffin | 10.0 |
| Beeswax | 2.0 |
| Polysorbate 60 | 0.6 |
| Sorbitan sesquiolate | 2.5 |
| Squalane | 3.0 |
| 1,3-Butylene glycol | 3.0 |
| Glycerine | 5.0 |
| Triethanolamine | 0.5 |
| Tocopheryl acetate | 0.5 |
| Preservative and pigment | adequate |
| Perfume | adequate |
| Purified water | residual |
| Total | 100 |

Formulation Example 3

Nourishing Lotion

Nourishing lotion containing the peptide nanosomes prepared in Example 2 was prepared according to a commonly employed method as follows.

TABLE 4

| Ingredients | Content (wt %) |
| --- | --- |
| Peptide nanosomes | 0.002 |
| 1,3-Butylene glycol | 4.0 |
| Glycerine | 4.0 |
| Cetearyl alcohol | 0.8 |
| Glyceryl stearate | 1.0 |
| Triethanolamine | 0.13 |
| Tocopheryl acetate | 0.3 |
| Liquid paraffin | 5.0 |
| Squalane | 3.0 |
| Macadamia nut oil | 2.0 |
| Polysorbate 60 | 1.5 |
| Sorbitan sesquiolate | 0.5 |
| Carboxyvinyl polymer | 1.0 |
| Preservative and pigment | adequate |
| Perfume | adequate |
| purified water | residual |
| Total | 100 |

Formulation Example 4

Essence

Essence containing the peptide nanosomes prepared in Example 2 was prepared according to a commonly employed method as follows.

TABLE 5

| Ingredients | Content (wt %) |
| --- | --- |
| Peptide nanosomes | 0.005 |
| Glycerine | 10.0 |
| 1,3-Butylene glycol | 5.0 |
| PEG 1500 | 2.0 |
| Allantoin | 0.1 |
| D/L-Panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanolamine | 0.18 |
| Octyldodeceth-16 | 0.4 |
| Ethanol | 6.0 |
| Perfume, preservative and pigment | adequate |
| Purified water | residual |
| Total | 100 |

Formulation Example 5

Hair Serum

Hair serum containing the peptide nanosomes prepared in Example 2 was prepared according to a commonly employed method as follows.

TABLE 6

| Ingredients | Content (wt %) |
| --- | --- |
| Peptide nanosomes | 0.005 |
| Glycerine | 7 |
| 1,3-Butylene glycol | 5.0 |
| PEG 1500 | 2.0 |
| Allantoin | 0.2 |
| D/L-Panthenol | 0.3 |
| EDTA-2Na | 0.02 |
| Hydroxyethyl cellulose | 0.2 |
| Sodium hyaluronate | 3.0 |
| Carboxyvinyl polymer | 0.5 |
| Triethanolamine | 0.18 |
| Octyldodeceth-16 | 0.4 |
| Ethanol | 4.0 |
| Perfume, preservative and pigment | adequate |
| Purified water | residual |
| Total | 100 |

Example 3

Hair Growth Promoting Effect of Synthesized Peptide

Figure 10:
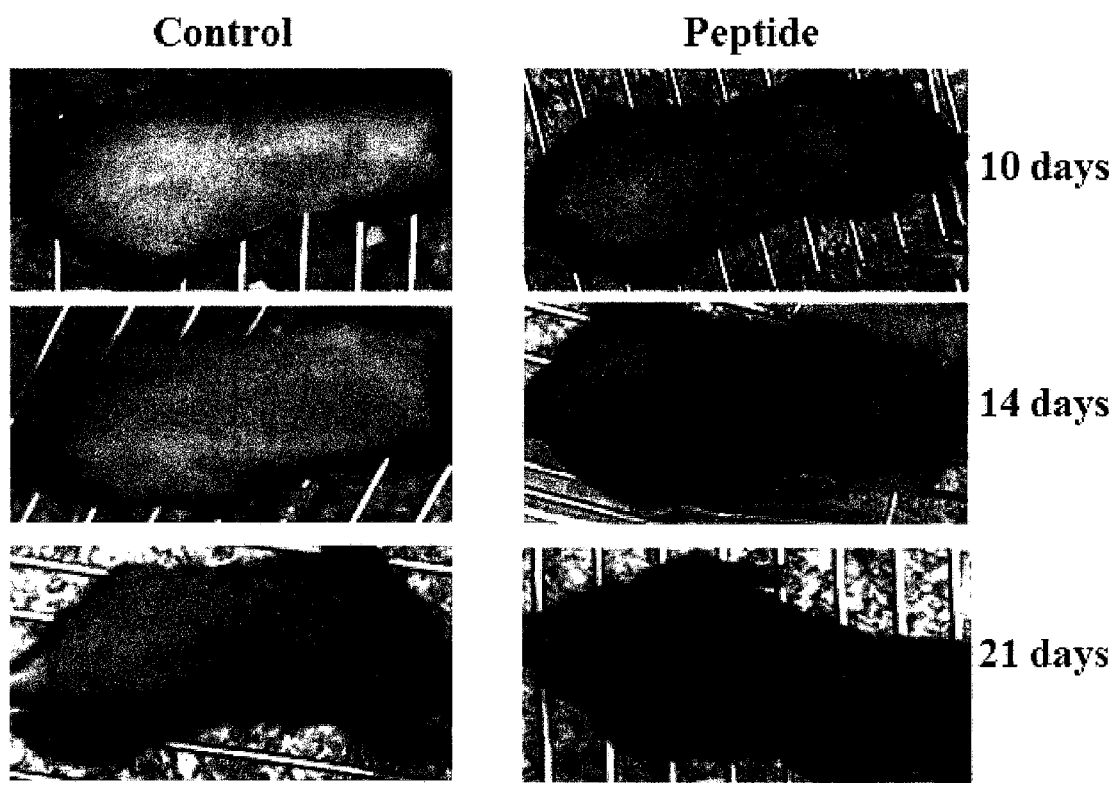
FIG. 10 shows a hair growth promoting effect on the back skin of a mouse treated with a peptide of the present disclosure.

In order to investigate the hair growth promoting effect of the peptide synthesized in Synthesis Example, hair of the back of a mouse (C57BL/6, Jung Ang Lab. Animal, Korea) was partially removed using hair removal cream. 10 μL of the peptide of SEQ ID NO: 1 (1 μg/μL) was administered or applied on the upper portion of the back of the mouse, and 10 μL of PBS was administered or applied on the lower portion of the back of the mouse, on days 0, 2 and 4. For each case, hair growth state was observed for 10 days. The peptide of the present disclosure was effective in promoting hair growth of the mouse (FIG. 10).

While the present disclosure has been described with respect to the specific embodiments, it will be apparent to those skilled in the art that various changes and modifications may be made without departing from the spirit and scope of the disclosure as defined in the following claims.

What is claimed is:

1. A peptide comprising the amino acid sequence of the general formula (1): SEQ ID NO:2-linker-SEQ ID NO:3 (1)
   wherein the linker comprises Xaa(n); Xaa is any amino acid; and n is an integer of 2-18;
   wherein the peptide exhibits an antagonistic activity against bone morphogenetic protein (BMP)-2, BMP-4 or BMP-7 by binding to BMP-2, BMP-4 or BMP-7.

2. The peptide according to claim 1, wherein the linker comprises 2 to 10 Gly residues.

3. The peptide according to claim 1, wherein the peptide has an ability to promote the growth of keratinocytes or fibroblasts.

4. The peptide according to claim 1, wherein the peptide promotes the production of laminin or hyaluronic acid in fibroblasts.

5. A composition comprising the peptide according to claim 1 as an active ingredient.

6. A method for promoting hair growth, comprising administering to a subject in need thereof a composition comprising the peptide according to claim 1 as an active ingredient.

* * * * *